United States Patent [19]

Dorr et al.

[11] Patent Number: 5,057,101
[45] Date of Patent: Oct. 15, 1991

[54] FEMORAL PROSTHESIS WITH CENTERING SLEEVE

[75] Inventors: Lawrence D. Dorr, Flint Ridge, Calif.; Marc M. Vreede, Northville, Mich.

[73] Assignee: Intermedics Orthopedics, Inc., Austin, Tex. ; a part interest

[21] Appl. No.: 561,461

[22] Filed: Aug. 1, 1990

[51] Int. Cl.$^5$ .......................... A61F 2/36; A61F 2/30
[52] U.S. Cl. ........................................ 623/23; 623/18
[58] Field of Search ...................... 623/23, 22, 20, 18, 623/16

[56] References Cited

U.S. PATENT DOCUMENTS

| | | | |
|---|---|---|---|
| 4,718,916 | 1/1988 | Morscher | 623/23 |
| 4,783,192 | 11/1988 | Wroblewski et al. | 623/23 X |
| 4,908,032 | 3/1990 | Keller | 623/23 X |

FOREIGN PATENT DOCUMENTS 0187903  7/1986  European Pat. Off. ............. 623/23

Primary Examiner—Ronald Frinks
Attorney, Agent, or Firm—John R. Merkling

[57] ABSTRACT

An apparatus for removably attaching a sleeve to a stem of a femoral prosthesis. The stem has a tapered portion midway along the stem rather than along the complete length of the stem or near the tip of the stem. There is a corresponding tapered portion on an inside surface of the sleeve near one end of the sleeve only.

9 Claims, 2 Drawing Sheets

FEMORAL PROSTHESIS WITH CENTERING SLEEVE

BACKGROUND OF THE INVENTION

My invention relates to femoral prostheses and in particular to apparatus for centering a stem of such a prosthesis in the medullary canal of a femur.

Various types of femoral prostheses are known and are used for surgical reconstruction of a femur. In general, these prostheses comprise a ball-shaped head mounted at an anatomical angle on a shank. The shank can be thrust into a medullary canal of a femur to mount the prosthesis on a reserved surface of the femur. Various means of fixation are known, including bone cement, areas of the prosthesis which promote bony ingrowth, and shoulders proximal to the head for preventing the prosthesis from wedging into the medullary canal.

Femoral prostheses are provided in a range of sizes. However, the variation in human anatomy is generally greater than the range of sizes available, or the range of sizes which can be reasonably stocked. To increase the variability of the available of sizes of protheses, sleeves have been proposed which can be placed on the shank of the prosthesis. These sleeves can be of varying thickness and tend to center the shank of the prosthesis in the medullary canal.

SUMMARY OF MY INVENTION

My invention relates particularly to an apparatus for removably attaching a sleeve to a stem of a femoral prosthesis. I have found that an improved fixation for a stem can be achieved by providing a tapered portion on the stem, midway along the stem, rather than along the complete length of the stem or near the tip of the stem. I provide a corresponding tapered portion on an inside surface of the sleeve near one end of the sleeve only. This configuration tends to allow a sleeve to be placed on the stem without excessive force. Moreover, the sleeve tends to be accurately placed along the length of the stem.

It is an object of my invention, therefore, to provide a femoral head prosthesis with removable sleeves which can be accurately placed on the stem of the prosthesis.

Another object of my invention is to provide a sleeve for a femoral prosthesis which minimizes stresses associated with placing a sleeve on the stem. Another object of my invention is to provide a sleeve for a femoral prosthesis which has an internal taper at one end of the sleeve only and which mates with a corresponding taper on the stem of the prosthesis midway in the length of the stem.

These an other objects and advantages of my invention will become more apparent from the following detailed description taken in conjunction with the accompanying drawings.

DETAILED DESCRIPTION OF MY PREFERRED EMBODIMENT

Figure 1:
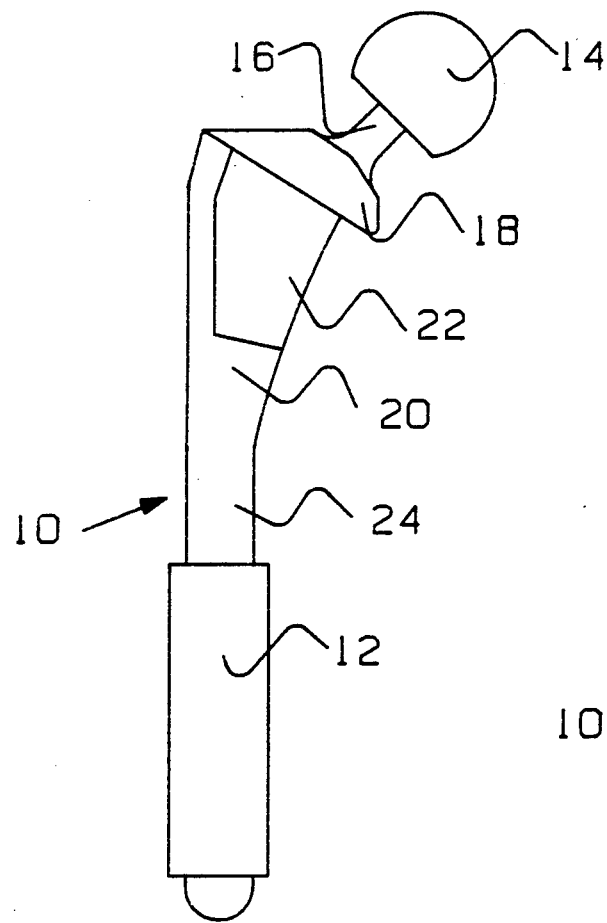
FIG. 1 is a plan view of a femoral prosthesis with a sleeve.
Figure 2:
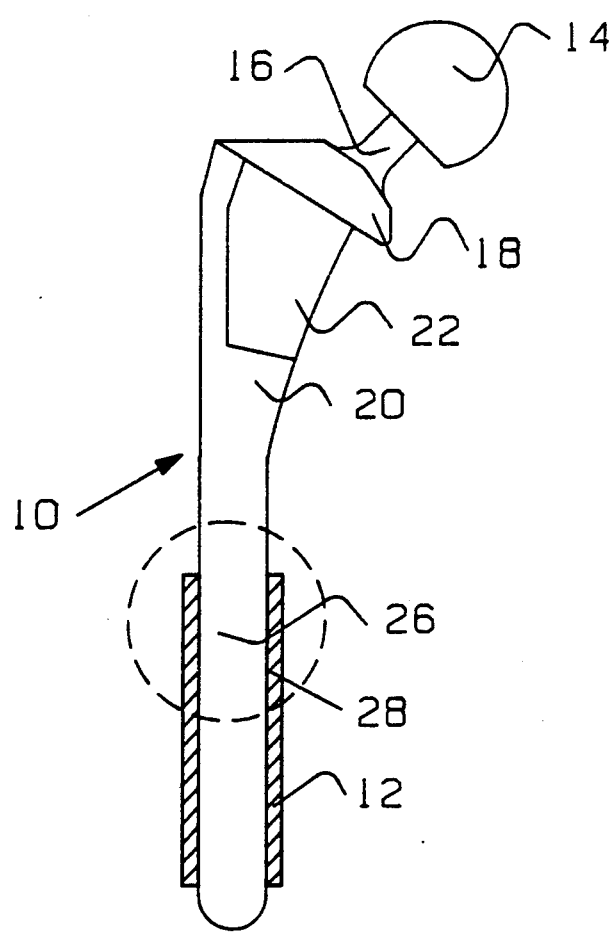
FIG. 2 is plan view of the prosthesis of FIG. 1 with the sleeve shown in section.
Figure 3:
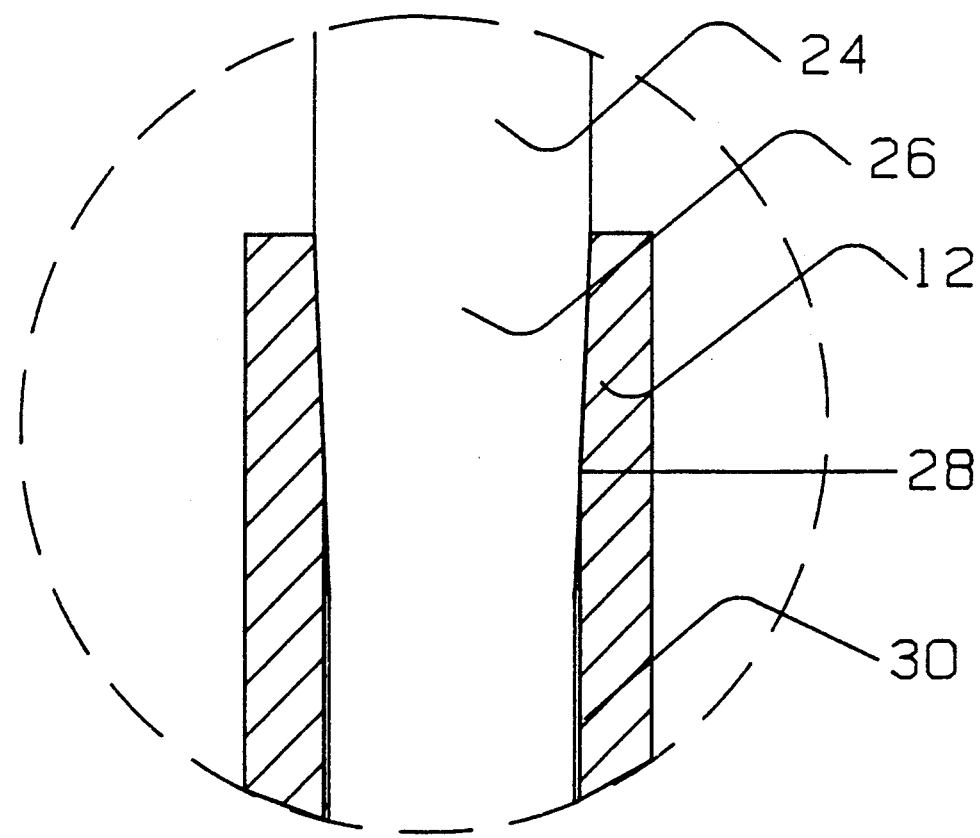
FIG. 3 is an enlarged portion of the sleeve and prosthesis of FIG. 2 illustrating mating tapers according to my present invention.

In referring to the accompanying drawings, like numerals will refer to like parts throughout the description. In FIG. 1, a femoral prosthesis 10 with a sleeve 12 is illustrated. I prefer a prosthesis having a generally spherical polished head 14 mounted on a tapered neck 16. The head 14 can be removed from the neck 16, so that various sizes of head can be used with a prosthesis. Adjacent the neck 16 is a shoulder 18 which generally prevents the prosthesis from wedging into a medullary canal of a femur, an action which occasionally splits a femur. Below the shoulder 18 is an enlarged portion 20 adapted to fill a cavity in the femur. A portion area 22 can be provided to promote fixation of the prosthesis in the femur. Below the enlarged portion 20 is a shank 24. In my preferred embodiment, the shank has a circular cross-section and is generally straight. To accommodate the curve in the medullary canal of the human femur, the enlarged portion 20 is generally bent with respect to the axis of the shank 24. The sleeve 12 is provided in a range of thicknesses. I prefer that it cover at least half of the length of the shank 24.

To affix the sleeve 12 to the shank 24 I have provided a male taper 26 located between the enlarged portion 20 and the middle of the length of the shank 24. Above the shank the taper 26, proximal to the enlarged portion 20, the shank has is a uniform diameter. Similarly, below the taper, at the distal portion of the shank, the shank's diameter is also uniform, but smaller than the diameter above the taper. Within sleeve 12, a corresponding female taper 28 is provided at the proximal end of the sleeve. This area should be about one-fifth of the overall length of the sleeve. The distal portion of the sleeve below the female taper 28 should have a uniform dimension, slightly larger than the diameter of the distal portion of the shank.

With the foregoing configuration, the sleeve can be effectively placed on the shank in only one direction. There remains a slight amount of space between an interior wall 30 of the sleeve and the distal portion of the shank. Consequently, a relatively long sleeve can be easily slid onto the shank and fixed replicably at a selected location on the shank.

My invention may be embodied in other specific forms without departing from the spirit or essential characteristics thereof. The present embodiment is therefore considered in all aspects as illustrative and not restrictive, the scope of my invention being indicated by the appended claims rather than by the foregoing description, and all changes which come within the meaning and range of equivalency of the claims are therefore intended to be embraced therein.

I claim as my invention:

1. A femoral head prosthesis comprising
a generally circular head;
an enlarged portion distal from the head for insertion into a cavity in a patient's femur;
a shank distal from the enlarged portion for extending into a medullary canal of the femur, and
a sleeve adapted to fit over the shank for varying the effective diameter of the shank, the shank comprising means for engaging the sleeve, said engaging means comprising a male taper located between the enlarged portion and the midpoint of the length of the shank, and sleeve comprising an interior surface having a female taper for attaching the sleeve at the engaging means, said female taper comprising about one-fifth of said interior surface of the sleeve.

2. The femoral head prosthesis according to claim 1, wherein the shank comprises a proximal portion of the shank adjacent the enlarged portion, said proximal portion having a first constant cross-section; and a distal portion of the shank, said distal portion having a second constant cross-section smaller than the first cross-section, and wherein said tapered portion of the shank is intermediate the first and second portions.

3. The femoral head prosthesis according to claim 2, wherein the first and second cross-sections are circles.

4. The femoral head prosthesis according to claim 3, wherein the distal portion of the shank has a length equal to or longer than the length of the proximal portion of the shank.

5. The femoral head prosthesis according to claim 4, wherein the shank is straight.

6. A femoral head prosthesis comprising
a generally circular head;
an enlarged portion distal from the head for insertion into a cavity in a patient's femur;
a cylindrical shank distal from the enlarged portion for extending into a medullary canal of the femur,
a sleeve having a cylindrical interior surface adapted to fit over the shank for varying the effective diameter of the shank, the shank comprising means for engaging the sleeve, said engaging means comprising a male taper located between said enlarged portion and the mid point of the length of the shank, the interior surface of the sleeve having a female taper, said female taper comprising about one-fifth of said interior surface of the sleeve.

7. The femoral head prosthesis according to claim 6, wherein the shank comprises a proximal portion of the shank adjacent the enlarged portion, said proximal portion having a first constant circular cross-section, and a distal portion of the shank, said distal portion having a second constant circular cross-section smaller than the first cross-section and wherein said tapered portion of the shank is intermediate the first and second portions.

8. The femoral head prosthesis according to claim 7, wherein the distal portion end of the shank has a length equal to or longer than the length of the proximal portion of the shank.

9. The femoral head prosthesis according to claim 8, wherein the shank is straight.

* * * * *